United States Patent [19]

Brill, III

[11] Patent Number: 4,901,578

[45] Date of Patent: Feb. 20, 1990

[54] PROBE CARRIER DRIVE ASSEMBLY

[75] Inventor: Bernard A. Brill, III, Bellevue, Pa.

[73] Assignee: Westinghouse Electric Corp., Pittsburgh, Pa.

[21] Appl. No.: 196,719

[22] Filed: May 20, 1988

[51] Int. Cl.⁴ .............................................. G01N 29/04
[52] U.S. Cl. ........................................................ 73/623
[58] Field of Search ............... 73/618, 623, 621, 866.5

[56] References Cited

U.S. PATENT DOCUMENTS

| | | | |
|---|---|---|---|
| 3,831,084 | 8/1974 | Scalese et al. | 324/40 |
| 3,906,358 | 7/1975 | Stone | 324/37 |
| 3,926,040 | 12/1975 | Cowell | 73/67.8 |
| 4,087,748 | 5/1978 | Pigeon et al. | 324/220 |
| 4,523,470 | 6/1985 | Muller et al. | |
| 4,597,294 | 7/1986 | Brill, III et al. | 73/623 |
| 4,624,400 | 11/1986 | Zimmer | |
| 4,772,849 | 9/1988 | Tedder | 73/623 |

OTHER PUBLICATIONS

Co-pending patent application Ser. No. 26,363, filing date Mar. 16, 1987, in the name of James W. Everett entitled "Double Gimbal Camlock Installation Assembly", assigned to the Westinghouse Electric Corporation.

NUCON Engineering and Control B.V., Inspection and Plant Services, "Inspection of Steam Generator Tubes with Ultrasonic Technique (The NUCON Nerason System)", Document No. I9530-00-003, Issue No. 3, Feb. 1986.

Inland Motor, Division Kollmorgan Corp. sales brochures, "High Performance DC Brushless Motors 01200 Series" and Brushless Motors Application Guide.

Primary Examiner—John Chapman
Assistant Examiner—Michele Simons
Attorney, Agent, or Firm—Walter S. Stevens

[57] ABSTRACT

Probe carrier drive assembly for moving a probe carrier without slip or creep in a steam generator tube so that a probe, which has an inspection device attached thereto and which is connected to the probe carrier, selectively rotates in place, follows a linear scanning path through the tube or follows a helical scanning path having a variable pitch. The probe carrier drive assembly comprises an elongated circular member and a drive mechanism engaging the elongated circular member for moving the elongated circular member axially and rotatably within the tube. The drive assembly further comprises motors coupled to the drive mechanism for operating the drive mechanism and includes a controller operatively coupled to the motors for operating the motors so that the elongated circular member selectively rotates in place, follows a linear path in the tube or follows a helical path having a variable pitch.

33 Claims, 9 Drawing Sheets

PROBE CARRIER DRIVE ASSEMBLY

BACKGROUND OF THE INVENTION

This invention relates generally to an inspection mechanism for detecting flaws in tubing and more specifically relates to a probe carrier drive assembly for moving a probe carrier without slip or creep in a steam generator tube so that a probe, which has an inspection scanning device attached thereto and which is connected to the probe carrier, selectively rotates in place in the tube, follows a linear scanning path through the tube or follows a helical scanning path having a variable pitch.

It is well known that a steam generator is a device for generating steam when heat is transferred by conduction through a heat conductor boundary separating a primary fluid from a secondary fluid, wherein the secondary fluid is water and wherein the primary fluid obtains a higher temperature than the secondary fluid. As the temperature of the secondary fluid increases, the secondary fluid reaches saturation temperature beyond which saturation temperature increasing fractions of the secondary fluid enter the vapor phase thereby producing steam. Typically, the steam generator includes a plurality of conduits or tubes through which the primary fluid flows, the walls of which tubes function as the heat conductor boundary for conducting heat from the primary fluid to the secondary fluid.

In a nuclear reactor the primary fluid flowing in the steam generator tubes is radioactive water; hence, the steam generator is designed such that the radioactive primary fluid does not radioactively contaminate the secondary fluid by intermixing with the secondary fluid. It is therefore desirable that the tubes remain leak-tight so that radioactive primary fluid remains everywhere separated from the secondary fluid to avoid intermixing the radioactive primary fluid with the secondary fluid.

Occasionally due to tube wall defects or tube wall cracking caused by stress and corrosion during operation, the steam generator tubes may develop surface and volume flaws and thus may not remain leak-tight. More specifically, laboratory tests have indicated that the defects or cracking referred to above may be due to a combination of the high temperature of the primary fluid, the conditions of stress and strain resulting from hard rolling the tubes and a possible susceptibility of the tubing material microstructure to experience intergranular stress and corrosion during operation. If through wall cracking occurs, some of the steam generator tubes may not remain leak-tight. Therefore, it is customary to inspect the tubes for flaws or irregularities so that corrective action may be taken to ensure that the primary fluid does not intermix with the secondary fluid. Such corrective action may be to plug or sleeve the tubes having flaws or irregularities.

However, before corrective action is taken it is prudent to first determine which steam generator tubes have flaws or irregularities. As well known in the art of nondestructive examination, determination of which tubes have flaws or irregularities requiring corrective action may be performed by inspecting the suspect tubes using an eddy current and/or ultrasonic transducer inspection device which is capable of electronically and/or sonically scanning the suspect tube. When an ultrasonic transducer is used, the ultrasonic transducer is coupled to the tube wall by a suitable couplant, such as water. The ultrasonic transducer signals, which pass through the couplant, are then reflected from the inner and outer surfaces of the tube wall and returned to the transducer and converted to electrical impulses which are transmitted to a measuring device. The reflected signals from the inner and outer surfaces of the tube wall are spaced apart in time by a time interval proportional to the thickness of the tube wall. The measuring device converts this difference in time to a voltage level indicating the thickness of the tube wall. The voltage level is then output to a display device for displaying the variation in tube wall thickness at various locations along the tube wall. Eddy current techniques, on the other hand, are based on the well known principle that when an electrical conductor is placed in an alternating magnetic field, eddy currents are generated in the conductor by electromagnetic induction. The magnitude and phase of these currents are a function of the electrical conductivity and physical characteristics of the conductor. These eddy currents produce a magnetic field which may be detected and measured. Thus, an eddy current probe carrier, which includes a test coil to which an oscillating current is applied, is moved along the tube and the effect on the electrical impedance of the test coil is measured to provide an indication of the physical characteristics of the tube. Of course, to scan the tube in a predetermined manner for flaws or irregularities the ultrasonic transducer and/or eddy current device should be suitably moved in the predetermined scanning pattern along the inside surface of the tube longitudinally within the tube.

It is the usual practice in the art to include the ultrasonic transducer and/or eddy current device in a probe connected to an elongated probe carrier, which probe and probe carrier are capable of being inserted into and moved along the inside surface of the tube to be inspected. The probe carrier is in turn engaged by a probe carrier drive which may engage the probe carrier by friction rollers. However, the use of friction rollers can subject the probe carrier to slip and creep; thus, a problem in the art has been to provide a probe carrier drive that allows the probe to be accurately moved in the desired manner without slip or creep within the tube to be inspected.

Moreover, another problem in the art has been to provide a probe carrier drive capable of engaging the probe carrier such that the probe carrier and connected probe selectively rotate in place in the tube, follow a linear scanning path in the tube or follow a helical scanning path having a variable pitch. Moving the probe carrier and probe in this manner allows the desired amount of data regarding the thickness of the tube wall to be obtained. Although the prior art may disclose probe carrier drives which allow the probe carrier and probe to rotate in place, to follow a helical scanning path or to follow a linear scanning path, a problem frequently encountered in the art is to provide a probe carrier drive which allows the probe carrier and probe to follow a helical scanning path having a variable pitch and to provide a probe carrier which moves within the tube without slip or creep.

There are several devices known in the art for moving a probe carrier and probe in a tube. One such device is disclosed by U.S. Pat. No. 3,831,084 issued August 20, 1974 in the name of Joseph J. Scalese et al. and entitled "Probe Carrier With Means For Selectively Permitting A Stationary Or A Helical Scan". This patent discloses a helically scanning eddy current flaw detector having a controllable sleeve which allows the detector to selectively either follow a helical scanning path or rotate in place. However, the Scalese et al. device does not appear to allow the detector to follow either a linear scanning path without helical motion or to follow a helical scanning path having a variable pitch.

Another device for moving a probe carrier in a tube is disclosed by U.S. Pat. No. 3,926,040 issued Dec. 16, 1975 in the name of Thomas E. Cowell and entitled "Device For Guiding Sensor Movement Within A Tube". The Cowell device relates to precisely repositioning a sensor within a tube such as a nuclear reactor vessel component in order to accomplish nondestructive testing, such as inspection of the tubular interior wall for flaws. The Cowell device comprises an elongated carrier pipe extending through a drive gear and further comprises a working head secured to the carrier pipe. A first reversible motor is operatively coupled with the drive gear to cause rotation of the carrier pipe. A second reversible motor is connected to the drive gear and operatively coupled to a gear rack to selectively cause axial movement of the carrier pipe. Actuator means is provided to operate the first reversible motor and second reversible motor either separately or simultaneously to thereby cause movement of the carrier pipe and repositioning of the working head within the tube. The Cowell device, however, does not appear to allow the carrier pipe to follow a helical scanning path having a variable pitch in the manner of the present invention.

Yet another device for moving a probe carrier in a tube is disclosed by U.S. Pat. No. 4,624,400 issued Nov. 25, 1986 in the name of John J. Zimmer entitled "Electromagnetic Probe Carrier Drive Apparatus" and assigned to the Westinghouse Electric Corporation. The Zimmer patent is directed towards an apparatus for driving a probe connected to an elongated flexible probe carrier. The apparatus comprises a rotatable drive member having an endless drive surface and means for holding the probe carrier in frictional engagement with the drive surface. However, the Zimmer patent does not appear to disclose means for rotating the probe carrier in place or moving the probe carrier without slip or creep in a helical scanning path having a variable pitch.

Consequently, while the prior art discloses devices for moving a probe carrier and connected probe in a tube, the prior art does not appear to disclose a device which moves a probe carrier without slip or creep in a tube such that the probe carrier and probe selectively rotate in place, follow a linear scanning path, or follow a helical scanning path having a variable pitch.

Therefore, what is needed is a probe carrier drive assembly for moving a probe carrier and probe without slip or creep in a steam generator tube so that the probe, which has an inspection device attached thereto and which is connected to the probe carrier, selectively rotates in place, follows a linear scanning path through the tube, or follows a helical scanning path having a variable pitch.

SUMMARY OF THE INVENTION

Disclosed herein is a probe carrier drive assembly for moving a probe carrier without slip or creep in a steam generator tube so that a probe, which has an inspection device attached thereto and which is connected to the probe carrier, selectively rotates in place, follows a linear scanning path through the tube or follows a helical scanning path having a variable pitch. Thus, the probe carrier, which engages the probe carrier drive assembly, is capable of moving the probe in virtually any predetermined scanning pattern in the tube to be inspected.

The probe carrier drive assembly of the present invention comprises an elongated externally threaded probe carrier having a drive slot extending through the threads along the longitudinal axis of the probe carrier. The drive assembly further comprises a first sleeve surrounding a portion of the probe carrier, wherein the first sleeve has a drive slot insert for matingly engaging the drive slot of the probe carrier and for rotatably moving the probe carrier in the tube. Also included in the drive assembly is a second sleeve surrounding a different portion of the probe carrier, wherein the second sleeve has internal threads for matingly engaging the external threads of the probe carrier and for axially moving the probe carrier in the tube. The first sleeve and the second sleeve are operatively coupled to a first reversible motor, which may be a variable speed first reversible motor, and to a second reversible motor, which may be a variable speed second reversible motor, respectively, for cooperatively rotating the first sleeve and the second sleeve. When only the first sleeve rotates, the probe carrier axially moves within the tube without slip or creep such that a helical scanning pattern is obtained having a pitch equal to the lead of the thread on the probe carrier and having a right hand or left hand helix depending on whether the thread on the probe carrier defines a right hand or a left hand helix. When only the second sleeve rotates, the probe carrier axially moves within the tube without rotation and without slip or creep. When both sleeves rotate at the same speed and in the same direction, the probe carrier rotates in place without axial movement. When the first sleeve and second sleeve rotate at different speeds, the probe carrier rotates and axially moves within the tube without slip or creep such that a helical scanning pattern having a variable pitch of either right hand or left hand orientation dependent on the relative speeds of the motors is obtained. Thus, the cooperative rotations of the first reversible motor and the second reversible motor determine whether the probe carrier and probe rotate in place, follow a linear scanning path through the tube or follow a helical scanning path having a variable pitch of either right hand or left hand orientation.

BRIEF DESCRIPTION OF THE DRAWINGS

While the specification concludes with claims particularly pointing out and distinctly claiming the subject matter of the invention, it is believed the invention will be better understood from the following description, taken in conjunction with the accompanying drawings wherein:

DESCRIPTION OF THE PREFERRED EMBODIMENT

Occasionally it is necessary to inspect steam generator tubes for surface and volume flaws by using a probe carrier having an inspection probe attached thereto, which probe carrier and probe are capable of traveling the inside surface of the tube to be inspected. The invention described herein is a probe carrier drive assembly for moving a probe carrier and attached probe without slip or creep in a steam generator tube so that the probe carrier and probe rotate in place in the tube, follow a linear scanning path through the tube or follow a helical scanning path having a variable pitch of right-hand or left-hand helix.

Figure 1:
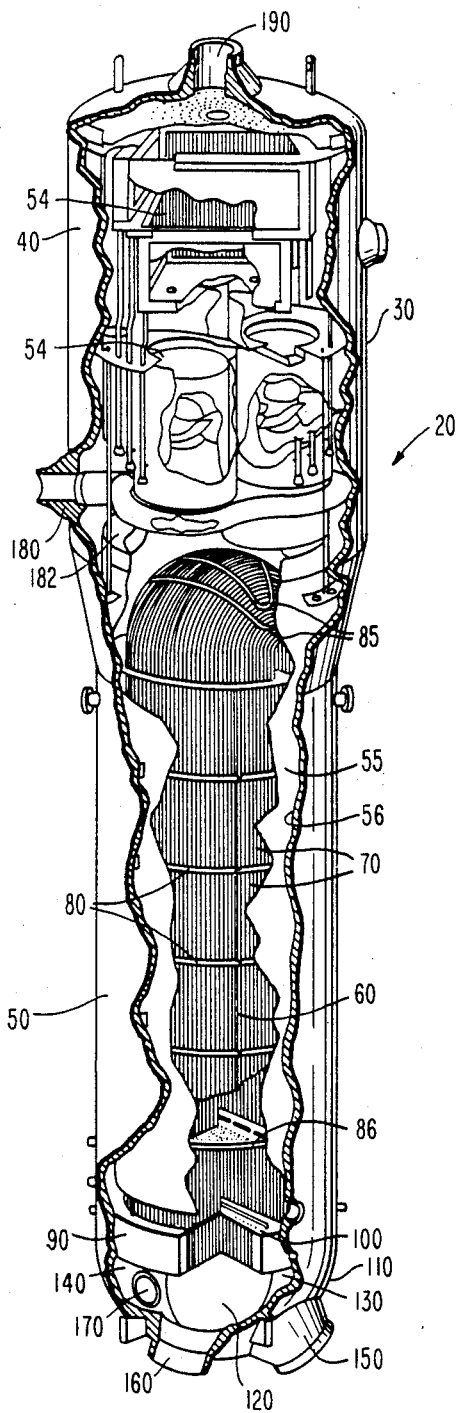
FIG. 1 is a view in perspective and partial vertical section of a steam generator with parts removed in the interest of clarity.

Referring to FIG. 1, a steam generator is referred to generally as 20 and comprises a generally cylindrical outer shell 30 having a cylindrical upper portion 40 and a cylindrical lower portion 50. Disposed in upper portion 40 is moisture separating means 54 for separating a steam-water mixture so that entrained water is removed from the steam-water mixture. Disposed in lower portion 50 is an inner shell 55 which is closed at its top end except for a plurality of openings disposed in its top end for allowing passage of the steam-water mixture from inner shell 55 to moisture separating means 54. Inner shell 55 is open at its bottom end, which inner shell 55 defines an annulus 56 between inner shell 55 and outer shell 30. Disposed in inner shell 55 is a vertical steam generator tube bundle 60 having a plurality of vertical, U-shaped steam generator tubes 70 therein, which may be mill annealed, thermally treated Inconel 600. Disposed at various locations along the length of bundle 60 are a plurality of horizontal, circular tube support plates 80, which may be Type 405 stainless steel, having holes therein for receiving each tube 70, for laterally supporting tubes 70 and for reducing flow induced vibration in tubes 70. Additional support for tubes 70 is provided in the U-bend region of bundle 60 by a plurality of anti-vibration bars 85 which may be chrome-plated Inconel.

Referring again to FIG. 1, disposed in lower portion 50 and below a bottom-most support plate 86 is a horizontal, circular tube sheet 90 having a plurality of vertical apertures 100 therethrough for receiving the ends of tubes 70, which ends of tubes 70 extend a predetermined distance through apertures 100. Tube sheet 90, which may be a nickel-molybdenum-chromium-vanadium alloy clad in Inconel, is sealingly attached, which may be by welding, around its circumferential edge to a hemispherical channel head 110. Disposed in channel head 110 is a vertical, semi-circular divider plate 120 sealingly attached, which may be by welding, to channel head 110 along the circumferential edge of divider plate 120. Divider plate 120 is also sealingly attached, which may be by welding, to tube sheet 90 along the flat edge of divider plate 120. Divider plate 120 divides channel head 110 into an inlet plenum chamber 130 and an outlet plenum chamber 140.

Still referring to FIG. 1, disposed on outer shell 30 below tube sheet 90 are a first inlet nozzle 150 and a first outlet nozzle 160 in fluid communication with inlet plenum chamber 130 and with outlet plenum chamber 140, respectively. A plurality of manway holes 170 are disposed on outer shell 30 below tube sheet 90 for providing access to inlet plenum chamber 130 and outlet plenum chamber 140. Disposed on outer shell 30 above tube bundle 60 is a second inlet nozzle 180, which is connected to a perforated, horizontal and generally toroidal feedring 182 disposed in upper portion 40 for allowing entry of nonradioactive secondary fluid into upper portion 40 through inlet nozzle 180 and through the perforations (not shown) of feedring 182. A second outlet nozzle 190 is disposed on the top of upper portion 40 for exit of steam from steam generator 20.

During operation of steam generator 20, radioactive primary fluid, which may obtain a temperature of approximately 620 degrees Fahrenheit, enters inlet plenum chamber 130 through first inlet nozzle 150 and flows through tubes 70 to outlet plenum chamber 140 where the primary fluid exits steam generator 20 through first outlet nozzle 160. The secondary fluid, which is water, enters feedring 182 through second inlet nozzle 180 which is connected to feedring 182 and flows downwardly from the perforations (not shown) of feedring 182 through annulus 56 until the secondary fluid is in fluid communication with tube sheet 90. The secondary fluid then leaves annulus 56 flowing upwardly by natural convection through bundle 60 where the secondary fluid boils and vaporizes into a steam-water mixture due to conductive heat transfer from the primary fluid to the secondary fluid through the walls of tubes 70 which comprise bundle 60 and which function as heat conductors. The steam-water mixture flows upwardly from bundle 60 and is separated by moisture separating means 54 into saturated water and dry saturated steam which may obtain a minimum quality of approximately 99.75 percent. The saturated water flows downwardly from moisture separating means 54 and mixes with the secondary fluid. Thus, as the secondary fluid enters second inlet nozzle 180 dry saturated steam exits steam generator 20 through second outlet nozzle 190. In a manner well known in the art, the dry saturated steam is ultimately transported to a heat sink (not shown) after the dry saturated steam exits steam generator 20 through second outlet nozzle 190. Moreover, in a nuclear reactor the primary fluid is radioactive; therefore, steam generator 20 is designed such that the primary fluid is nowhere in direct fluid communication with the secondary fluid in order that the non-radioactive secondary fluid is not radioactively contaminated by intermixing with the radioactive primary fluid.

Occasionally, due to tube wall defects or tube wall cracking caused by stress and corrosion, some tubes 70, for example a suspect steam generator tube 71 (see FIG. 2), may develop surface and volume flaws and thus may not remain leak-tight. Therefore, it is customary to inspect tube 71 to detect the location of and extent of flaws or irregularities (i.e., lack of bond in tube brazes) so that corrective action may be taken. Determination of whether tube 71 has flaws or irregularities sufficient to require corrective action may be obtained by examining tube 71 using a nondestructive examination scanning device (not shown). Naturally, the scanning device should be suitably moved without slip or creep along the inside surface of tube 71 so that tube 71 may be thoroughly scanned thereby for flaws or irregularities.

Figure 2:
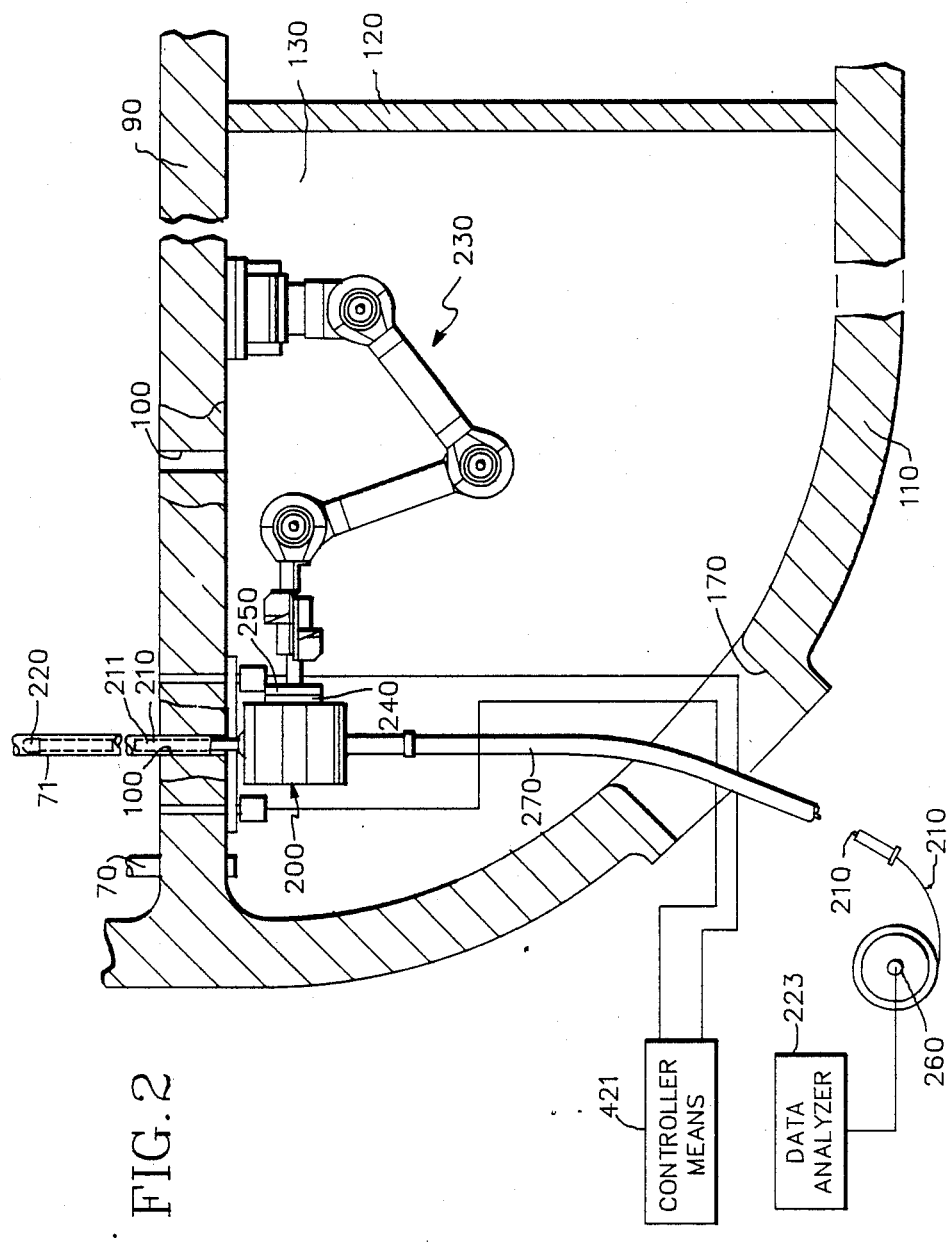
FIG. 2 illustrates a probe carrier drive assembly disposed in a plenum chamber of the steam generator beneath a steam generator tube to be inspected and releasibly connected to a remote service arm for positioning the drive assembly beneath the tube to be inspected.

Turning now to FIG. 2, there is illustrated the subject matter of the present invention which is a probe carrier drive assembly, generally referred to as 200, for suitably moving a probe carrier 210 without slip or creep in tube 71 so that a probe 220, which has a nondestructive examination scanning device attached thereto and which is connected to probe carrier 210, moves in a predetermined scanning pattern by selectively rotating in place in tube 71, following a linear scanning path in tube 71 or following a helical scanning path having a variable pitch. Probe carrier 210 may be a flexible, such as plastic, or nonflexible elongated circular drive shaft having a longitudinal hollow portion 222 (see FIG. 6) therethrough, wherein hollow portion 222 of probe carrier 210 is capable of receiving electrical wires therethrough that lead from the examination device and probe 220 to a data analyzer 223 which is capable of analyzing data received from the examination device regarding the physical characteristics of tube 71. As described in detail hereinafter, drive assembly 200 threadably engages probe carrier 210, which has external threads 224 thereon (see FIG. 5), such that probe carrier 210 and thus probe 220 precisely move without slip or creep in tube 71 in a predetermined scanning pattern for obtaining the desired data regarding the physical characteristics of tube 71. External threads 224 may be 29 degree stub tooth ACME threads for resisting abrasive wear on the distal ends of threads 224. Such stub tooth ACME threads are relatively shallow with respect to the base of the threads; therefore, such threads may be effectively used on relatively thin-walled flexible tubing for transmitting axial loads with minimal loss of tubing strength.

As shown in FIG. 2, disposed in inlet plenum chamber 130 may be a bifurcated remote service arm generally referred to as 230, such as a Remotely Operated Service Arm (ROSA) available from Westinghouse Electric Corporation located in Pittsburgh, Pa., for positioning drive assembly 200 coaxially beneath tube 71 which is to be inspected. Of course service arm 230 need not be bifurcated; rather, service arm 230 may be of any convenient configuration or mechanism for positioning drive assembly 200 beneath tube 71. Service arm 230 may be releasibly engaged, such as by camlock devices (not shown), at one end thereof to the ends of some tubes 70, which are sufficiently near tube 71, for releasibly securing service arm 230 beneath tube sheet 90. Service arm 230 is capable of moving in 360 degree horizontal and vertical arcs for positioning drive assembly 200 beneath tube 71. Connected to the other end of service arm 230 is a male coupler (not shown), which may be circular, for releasibly coupling service arm 230 to drive assembly 200. Integrally attached to the external surface of drive assembly 200 is a flanged boss 240, which may be circular. A female coupler 250, which may circular, is fixedly attached to flanged boss 240 for matingly engaging the male coupler so that drive assembly 200 may be releasibly coupled to service arm 230. Of course the male coupler may alternatively be a female coupler when female coupler 250 is alternatively a male coupler.

As described in detail hereinafter, drive assembly 200 engages probe carrier 210 which may extend from a probe carrier coiler 260, through manway hole 170, through drive assembly 200 and into tube 71. Carrier coiler 260, which may be a circular reel having a groove extending around the marginal edge thereof for receiving probe carrier 210 therein, is capable of accommodating probe carrier 210 wrappingly about carrier coiler 260. Surrounding a portion of probe carrier 210 may be a suitably flexible probe carrier guide hose 270, connected to and extending from drive assembly 200 to near carrier coiler 260, for protecting probe carrier 210 from abrasively wearing against the edge of manway hole 170. Connected to and/or disposed in probe carrier 210 is probe 220, which may contain a nondestructive examination scanning device such as an ultrasonic and/or eddy current nondestructive examination scanning device for nondestructively examining tube 71 for surface and volume flaws. As described in more detail hereinafter, drive assembly 200 may be suspended beneath tube 71 by a support means connected to tubes 70, which support means may be at least one camlock apparatus generally referred to as 280 (see FIG. 3) having a generally cylindrical elastically deformable expansion collar 300 (see FIG. 3) thereon for expandably releasibly engaging the inside surface of tube 70 proximate tube 71 which is to be inspected.

Figure 4:
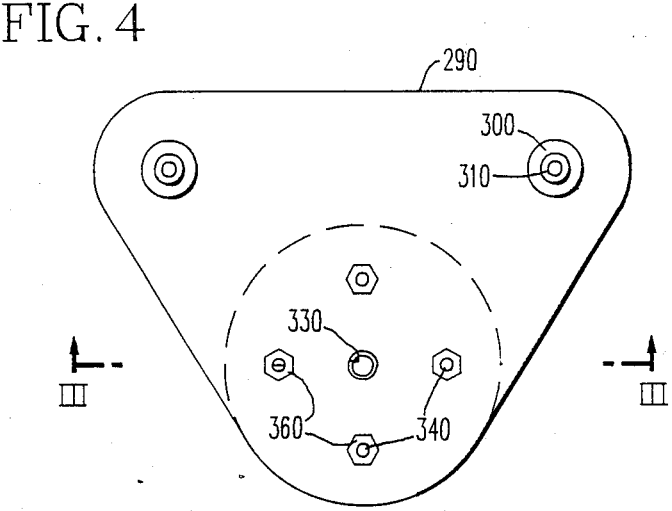
FIG. 4 is a view along section IV—IV of FIG. 3 showing the triangular configuration of a base plate which connects the camlock tools to the drive assembly.
Figure 3:
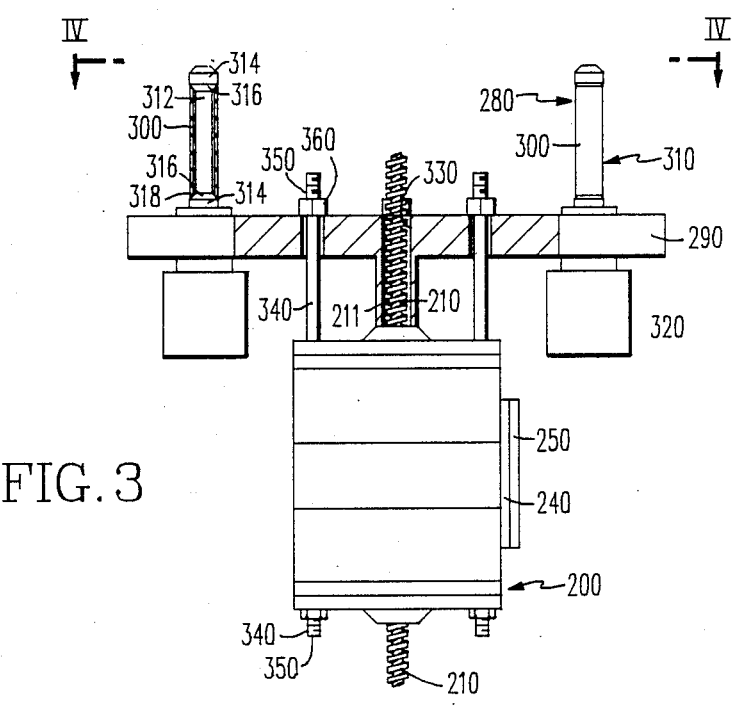
FIG. 3 is an illustration of the drive assembly connected to camlock tools which are capable of releasibly engaging steam generator tubes proximate the tube to be inspected for supporting the drive assembly beneath the tube to be inspected.

Referring to FIGS. 3 and 4, camlock apparatus 280 comprises a base plate 290, which may be a generally triangular-shaped member (see FIG. 4) having a T-shaped transverse cross section (see FIG. 3) for supporting at least one camlock tool generally referred to as 310 which is secured to base plate 290. Base plate 290 may be triangular-shaped for minimizing the volume of space occupied by base plate 290. As shown in FIG. 3, each camlock tool 310 comprises an elongated generally cylindrical plunger 312 having end caps 314 connected to each end thereof. Each end cap 314 includes a frusto-conical surface 316 on one end thereof for elastically deforming expansion collar 300 thereagainst. Surrounding plunger 312 is expansion collar 300 having inwardly inclining edges 318 for matingly abutting the opposing frusto-conical surface 316 of each end cap 314. When plunger 312 is axially translated toward base plate 290, frusto-conical surfaces 316 exert a compressive force against each opposing inclining edge 318 thereby compressively deforming and outwardly expanding expansion collar 300 for expandably releasibly engaging the inside surface of tube 70 proximate tube 71 so that drive assembly 200 is suspended beneath tube 71 by the force of friction acting at the interface of the outside surface of expansion collar 300 and the inside surface of tube 70. Conversely, when plunger 312 is axially translated away from base plate 290, the compressive force referred to immediately above is released thereby, such that expansion collar 300 elastically returns to its predeformed shape for disengaging expansion collar 300 from the inside surface of tube 70. Operatively coupled to plunger 312 is an electrical or gas-operated reversible camlock motor 320 for operating plunger 312 and thus expansion collar 300 so that expansion collar 300 expands and contracts for respectively engaging and disengaging the inside surface of tube 70. Moreover, extending through base plate 290 is a transverse bore 330 for receiving probe carrier 210 therethrough. Furthermore, as described in more detail presently, extending through drive assembly 200 is at least one spacer 340 having external threads 350 on each end thereof for maintaining base plate 290 in spaced-apart relation with respect to the top of drive assembly 200 and for connecting camlock apparatus 280 to drive assembly 200. Each of external threads 350 is capable of threadably engaging the internal threads of a nut 360 for attaching spacer 340 to drive assembly 200 and base plate 290.

Figure 5:
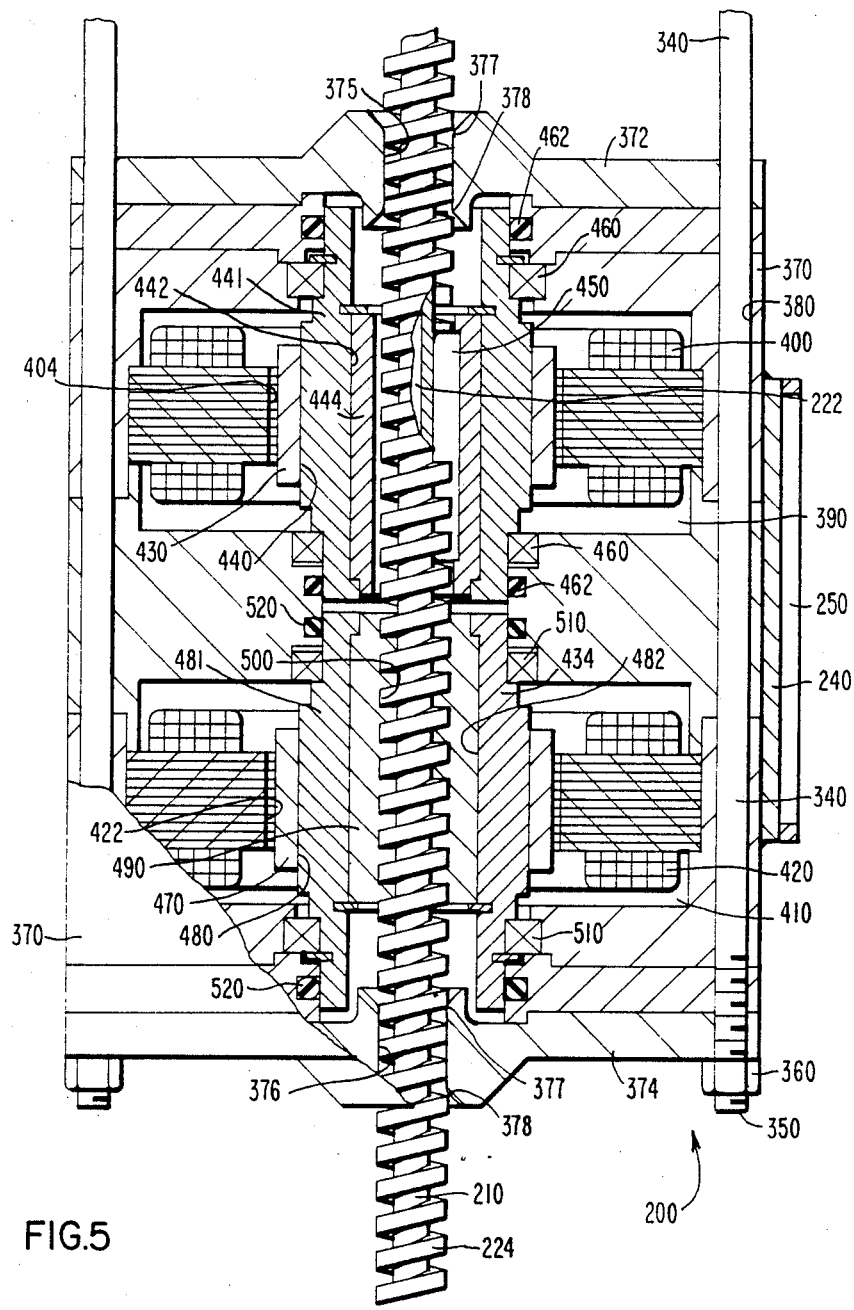
FIG. 5 is a view in partial vertical section of the drive assembly.

Referring now to FIG. 5, there is illustrated a drive assembly housing 370 for enclosing drive assembly 200 therein. Housing 370 may be a generally hollow cylinder having an open front end and an open rear end to provide access to the inside of housing 370 for performing maintenance and repair of drive assembly 200 which is disposed in housing 370. Housing 370 further comprises end cover plates 372 and 374 each removably attached to the open front end and the open rear end, respectively, of housing 370 for covering the open front end and the open rear end of housing 370 when drive assembly 200 is operating. End cover plates 372 and 374 have colinear passageways 375 and 376, respectively, for passage of probe carrier 210 therethrough. Moreover, each passageway 375 and 376 may include a first passageway shoulder 377 and a second passageway shoulder 378 for minimizing scratching, wearing, and binding of probe carrier 210 in passageways 375 and 376 when probe carrier 210 traverses through passageways 375 and 376. Thus, as illustrated in FIG. 5, first passageway shoulder 377 and second passageway shoulder 378 function as lead chamfers for suitably contacting probe carrier 210. Formed longitudinally through housing 370 is at least one housing channel 380 for receiving each associated spacer 340 therethrough.

As shown in FIG. 5, integrally attached to the external surface of housing 370 is flanged boss 240. Flanged boss 240 is attached to female coupler 250, which female coupler 250 is capable of matingly engaging the male coupler connected to service arm 230. Service arm 230 is in turn capable of positioning drive assembly 200 coaxially beneath tube 71. Formed in housing 370 is a first chamber 390 for receiving a first reversible motor 400, which may be a variable speed first reversible motor having a first hollow center 404 therethrough coaxially disposed with respect to passageways 375 and 376. First reversible motor 400 is disposed in first chamber 390 and connected therein to housing 370. Also formed in housing 370 is a second chamber 410 for receiving a second reversible motor 420, which may be a variable speed second reversible motor, having a second hollow center 422 therethrough coaxially disposed with respect to passageways 375 and 376. Second reversible motor 420 is disposed in second chamber 410 and connected therein to housing 370. As described hereinbelow, first reversible motor 400 and second reversible motor 420 are capable of driving probe carrier 210 and thus probe 220 in a predetermined scanning pattern along the inside surface of tube 71. Control of first reversible motor 400 and second reversible motor 420 may be provided by controller means 421 (see FIG. 2) operatively coupled to first reversible motor 400 and to second reversible motor 420 for selectively operating first reversible motor 400 and second reversible motor 420 so that the desired scanning path is obtained. First reversible motor 400 and second reversible motor 420 may have Hall effect devices (not shown) connected thereto for motor commutation and position feedback. When used for position feedback, the Hall effect devices may be operatively connected to first reversible motor 400 and to second reversible motor 420 for providing data to controller means 421 regarding the position of probe 220 in tube 71. Thus, controller means 421 is a two axis closed loop position controller. As well known in the art, Hall effect devices are sensors for detecting changes in the electro-magnetic field surrounding a motor coil. Such Hall effect devices may be used as a non-invasive means for determining changes in the movement and position of probe carrier 210. Moreover, other equivalent position encoding devices such as hollow center, frameless, brushless resolvers and hollow center optical encoders may be added or substituted in place of the Hall effect devices. Reversible motors 400 and 420 should be capable of producing relatively high torque for driving probe carrier 210 at high speed. In addition, reversible motors 400 and 420 may be adapted to utilize rare earth magnets and may be brushless for generating relatively less electrical noise to interfere with the signals from probe 220. Similarly, other hollow center motors or hollow center motors with in-line hollow center gear reducers may be substituted to meet torque, size, and cost constraints appropriate to a particular application.

Figure 7:
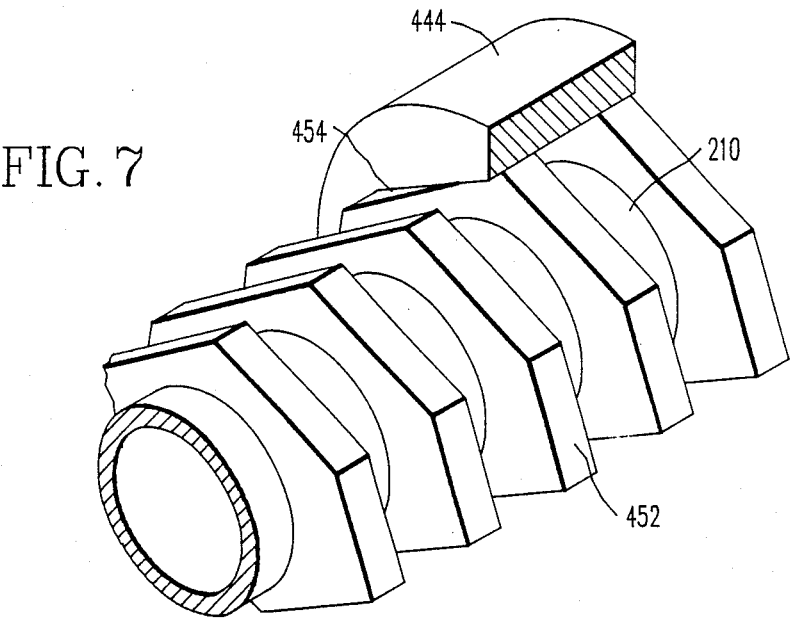
FIG. 7 is a view in perspective of the probe carrier having hexagonally-shaped helical threads.
Figure 8:
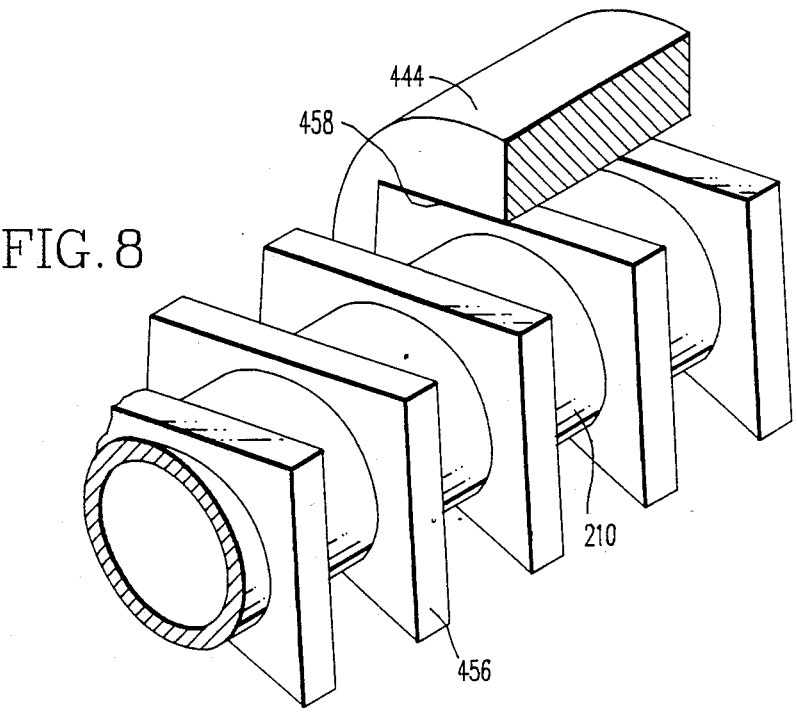
FIG. 8 is a view in perspective of the probe carrier having square-shaped helical threads.

Still referring to FIG. 5, disposed in first hollow center 404 is a cylindrical first rotor 430 having a longitudinal first opening 440 therethrough for receiving a cylindrical first liner 441 fixedly mounted therein. First liner 441 may be fixedly mounted in first opening 440 by a press fit. Moreover, liner 441 has a longitudinal first bore 442 therethrough for receiving a cylindrical first sleeve 444 removably mounted therein. It should be evident that first rotor 430 is capable of rotating when electrical current is applied to first reversible motor 400. As described in more detail hereinafter, first sleeve 444 has a generally rectangular-shaped drive shaft insert 450, which may be press fit into first sleeve 444, outwardly projecting from the inside surface of first sleeve 444 for rotatably matingly engaging a longitudinal drive slot 530 (see FIG. 6) which extends from near one end of probe carrier 210 to near the other end thereof for transmitting torque to probe carrier 210. Alternatively, drive shaft insert 450 may be deleted and torque transmitted instead by hexagonally-shaped threads 452 integrally formed about the length of probe carrier 210 (see FIG. 7). Hexagonally-shaped threads 452 rotatably matingly engage an associated hexagonally-shaped opening 454 formed through first sleeve 444 (see FIG. 7). The hexagonal shape of threads 452 allow a greater amount of torque to be transferred by first sleeve 444 to probe carrier 210 compared to the amount of torque that can be transferred when threads 224 are used. Moreover, drive shaft insert 450 may be deleted and torque transmitted instead by square-shaped threads 456 integrally formed about the length of probe carrier 210 (see FIG. 8). Square-shaped threads 456 matingly engage an associated square-shaped opening 458 formed through first sleeve 444 (see FIG. 8). The square shape of threads 456 allow a greater amount of torque to be transferred by first sleeve 444 to probe carrier 210 compared to the amount of torque that can be transferred when threads 224 are used. As shown in FIG. 5 disposed near each end of and contacting the eternal surface of first liner 441 is at least one first bearing 460 which is slidably interposed between housing 370 and first liner 441 near each end of first liner 441 for reducing frictional forces acting at the interface of first liner 441 and housing 370 when first liner 441 rotates in first opening 440. Also disposed near each end of and contacting the external surface of first liner 441 on the outboard side of first bearing 460 is at least one ring-shaped first seal 462 sealingly interposed between first liner 441 and housing 370, which first seal 462 may be an elastomeric seal for sealing first chamber 390 against liquid and particulate intrusion.

Again referring to FIG. 5, disposed in second hollow center 422 is a cylindrical second rotor 470 having a second opening 480 longitudinally therethrough for receiving a cylindrical second liner 481 fixedly mounted therein. Second liner 481 may be fixedly mounted in second opening 480 by a press fit. Second liner 481 has a longitudinal second bore 482 therethrough for receiving a cylindrical second sleeve 490 fixedly mounted therein. It will be understood that second rotor 470 is capable of rotating when electrical current is applied to second reversible motor 420. Second sleeve 490 has internal threads 500 for threadably engaging eternal threads 224 of probe carrier 210. As described in more detail hereinafter, second sleeve 490 functions as a threaded linear drive means threadably engaging external threads 224 of probe carrier 210 for axially moving probe carrier 210 in tube 71. The threaded engagement of internal threads 500 and external threads 224 is preferable to the use of friction rollers at that location because such threaded engagement inherently provides positive traction to move probe carrier 210 so that probe carrier 210 is capable of moving in tube 71 without slip or creep. The use of friction rollers, on the other hand, provides non-positive traction which may allow probe carrier 210 to slip and creep. Disposed near each end of and contacting the external surface of second liner 481 is at least one second bearing 510 which is slidably interposed between housing 370 and second liner 481 near each end of second liner 481 for reducing frictional forces acting at the interface of second liner 481 and housing 370 when second liner 481 rotates in second opening 480. Also disposed near each end of and contacting the external surface of second liner 481 on the outboard side of second bearing 510 is at least one ring-shaped second seal 520 sealingly interposed between second liner 481 and housing 370, which second seal 520 may be an elastomeric seal for sealing second chamber 410 against liquid and particulate intrusion.

Figure 6:
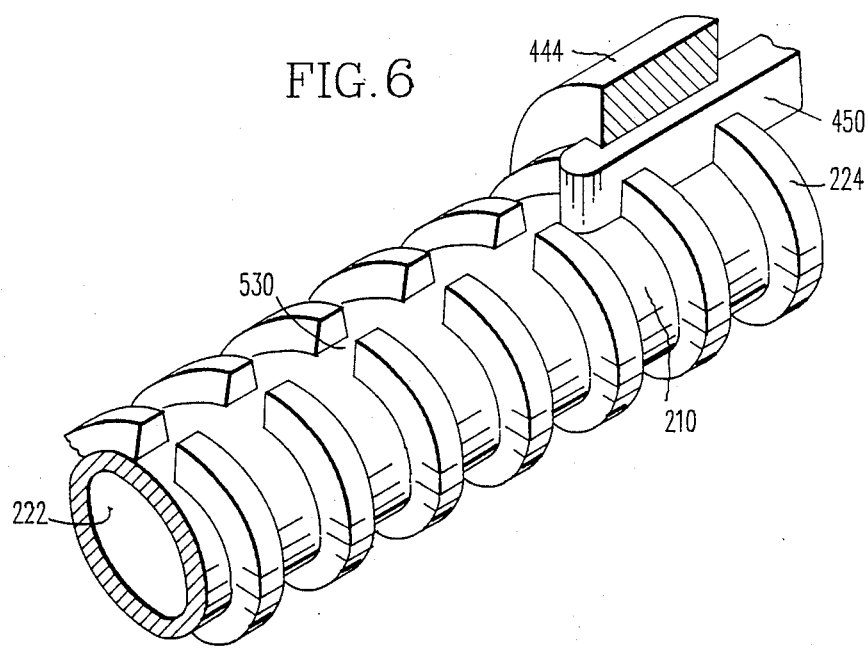
FIG. 6 is a view in perspective of an externally threaded probe carrier having a drive slot through the external threads thereof, which probe carrier is surrounded by a first sleeve having a rotary drive shaft insert inserted into the drive slot.

As best seen in FIG. 6, formed through external threads 224 of probe carrier 210 is drive slot 530, wherein drive slot 530 may be an elongated keyway longitudinally extending from near one end of probe carrier 210 to near the other end thereof for matingly engaging drive shaft insert 450 which outwardly projects from the inside surface of first sleeve 444 for rotatably matingly engaging drive slot 530. As stated above, probe carrier 210 may have hexagonally-shaped threads 452 (see FIG. 7) or square-shaped threads 456 (see FIG. 8) integrally formed about the length thereof, which threads 452 or 456 rotatably matingly engage associated opening 454 or 458, respectively, for transmitting increased torque to probe carrier 210.

Figure 9:
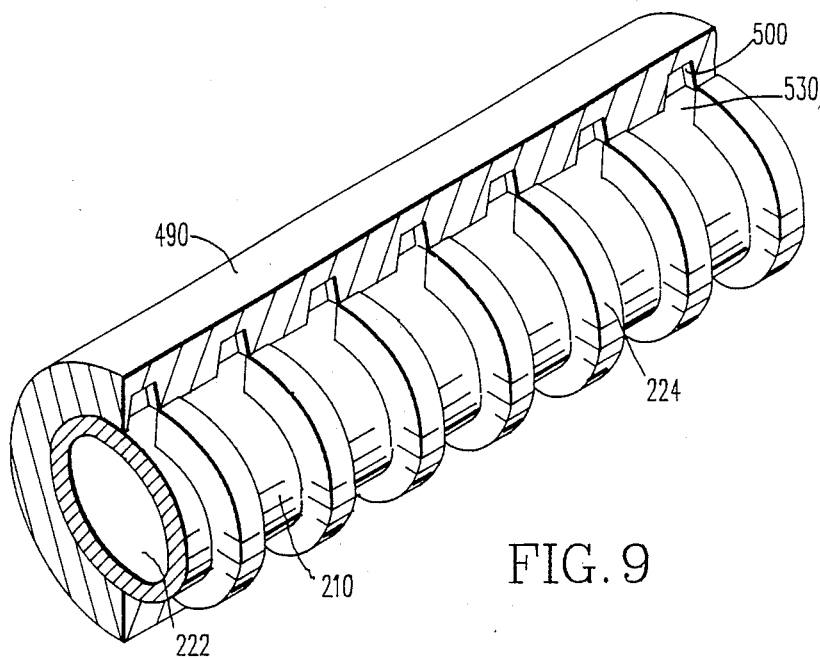
FIG. 9 is a view in perspective and longitudinal section illustrating the externally threaded probe carrier surrounded by an internally threaded second sleeve.

As shown in FIG. 9, second sleeve 490, which surrounds drive shaft 210 has internal threads 500 therein for threadably engaging external threads 224 of drive shaft 210. Internal threads 500 may be 29 degree stub tooth ACME threads for matingly engaging external threads 224, which also may be 29 degree stub tooth ACME threads.

As stated above, probe carrier 210, which has probe 220 attached thereto, selectively rotates in place in tube 71, follows a linear scanning path through tube 71 or follows a helical scanning path having a variable pitch. The scanning path of probe 220 is generally determined by the following basic equations of motion which describe the movement of probe carrier 210 and thus probe 220 through tube 71:

$$Ls = P_1 + P_2 + \ldots P_i + \ldots P_n; \quad (1)$$

in addition, $$Ls = \left| \left( \frac{Nk - Nt}{Nk} \right) Lb \right| \quad (2)$$

$$Va = (Nk - Nt) \frac{Lb}{60} \text{ and} \quad (3)$$

$$Vs = \sqrt{\left( \frac{Nk \pi D}{60} \right)^2 + \left[ \left( \frac{Nk - Nt}{60} \right) Lb \right]^2} \quad (4)$$

where,
$P_i$ = pitch in inches of transducer $T_i$ as i varies from 1 to the total number n of transducers attached to probe 220;
Nk = rotational speed of first sleeve 444 in drive assembly 200 in revolutions per minute;
Nt = rotational speed of second sleeve 490 in drive assembly 200 in revolutions per minute;
Lb = lead of the internal threads 500 of second sleeve 490 in inches;
Ls = lead of scan path in inches;
Va = speed of advance of probe carrier 210 along the longitudinal axis of tube 71 in inches per second;
Vs = surface speed of the impingement point of any scanning ray extending from the examination device to the surface of tube 71 in inches per second; and
D = diameter of the surface being scanned in inches.

With respect to the sign convention applicable to the above basic equations, Va and Vs are taken as positive when probe 220 advances from drive assembly 200 towards tube 71 and Va and Vs are taken as negative when probe 220 retreats from tube 71 towards drive assembly 200. The sign of Nk is positive and thus the sense of rotation of Nk is positive when the rotation is clockwise as viewed from the rear end of drive assembly 200 along the longitudinal axis thereof. Similarly, for counter-clockwise rotation the sign of Nk is negative. In the case of Nt, the sign of Nt is determined in the same manner as the sign of Nk. It will be appreciated that in the special case where a single transducer is connected to probe carrier 210, Ls is equal to the pitch of probe 220, which is the distance between scan lines measured on the inside surface of tube 71 parallel to the longitudinal axis of tube 71. However, when probe carrier 210 has more than one transducer connected thereto the pitch of probe 220 is less than the lead, Ls. In the above basic equations, it is assumed that second sleeve 490 has a right hand thread. A left hand thread may also be used without departing from the spirit of the invention, but the sign of Nt in each of the above basic equations would then be changed accordingly. The direction of rotation of probe carrier 210 is determined by the direction of rotation of first reversible motor 400 because first reversible motor 400 is operatively coupled to first sleeve 444 which has drive insert 450 rotatably matingly engaging drive slot 530 of probe carrier 210. Thus, probe carrier 210 rotates in the same direction as the direction of rotation of first sleeve 444. The direction of axial movement of probe carrier 210 is determined by whether internal threads 500, which threadably engage external threads 224, are right or left-hand threads and by the direction of rotation of first sleeve 444. The speeds of rotation and axial movement of probe carrier 210 and the scanning pattern are determined by the relative magnitudes of Nk an Nt.

When tube 71 is inspected, an operator of drive assembly 200 may require that probe 220 scan certain areas of tube 71 more thoroughly than other areas of tube 71. More specifically, the operator may require that tube 71 be scanned at a varying speed and pitch rather than at a constant speed and pitch. For example, probe 220, which may have an array of one or more ultrasonic and/or eddy current transducers attached thereto, may be operated such that probe 220 scans at a course lead resulting in a sampling inspection rather than at a fine lead resulting in a near 100% inspection. Thus, it should be evident from the basic equations of motion that the relative speeds of first reversible motor 400 and second reversible motor 420 and thus first sleeve 444 and second sleeve 490, respectively, may be changed by the operator when probe 220 reaches preselected locations in tube 71 to obtain a finer lead scan and more thorough inspection of those locations. Such locations in tube 71 may correspond to the regions of support plates 80 and anti-vibration bars 85.

Moreover, inspection time may be reduced or the extent of the inspection may be increased in several ways. For example, the parameters in the above basic equations may be suitably adjusted and/or the number of transducers in probe 220 may be increased. Alternatively, probe 220 may be guided along a right hand helix during advance of probe 220 into tube 71 and along a left hand helix during retreat of probe 220 from tube 71. With respect to the helical motion described immediately above, it will be appreciated that the respective scanning paths during advancement of probe 220 and retreat of probe 220 will cover different portions of the inside surface of tube 71 during the process of advancement of probe 220 and retreat of probe 220 so that a greater percentage of the inside surface is inspected.

In view of the above description, if more than one ultrasonic transducer and/or eddy current device is attached to probe 220, there will be additional scanning paths, equal to the number of ultrasonic transducers and/or eddy current devices, traced on the inside surface of tube 71. Thus, it follows that in the case of multiple scanning paths, there will be multiple corresponding pitches $P_i$. Of course, the special case of one ultrasonic transducer or eddy current device results in one scanning path and one pitch equal to the lead Ls.

The above basic equations of motion can be rewritten into particularized equations of motion as follows:

$$Ls = \left| \left(1 - \frac{Nt}{Nk}\right) Lb \right| \quad (5)$$

$$Va/Nk = \left(1 - \frac{Nt}{Nk}\right) \frac{Lb}{60} \text{ and} \quad (6)$$

$$Vs/\sqrt{Nk} = \sqrt{\left(\frac{\pi D}{60}\right)^2 + \left[\left(1 - \frac{Nt}{Nk}\right)\frac{Lb}{60}\right]^2} \quad (7)$$

where Nt, Nk, Lb, Va, Vs and D obtain the same unit dimensions as specified for the basic equations. Rewriting the basic equations of motion into particularized equations of motion more particularly defines Va, Vs, and Ls as functions of the ratio (Nt/Nk) of the speeds of second reversible motor 420 and first reversible motor 400. It is recalled that Ls is equal to the scanning pitch when one transducer is connected to probe 220. As indicated by Equation (1), Ls is also equal to the sum of the scanning pitches when more than one transducer is connected to probe 220.

Figure 10:
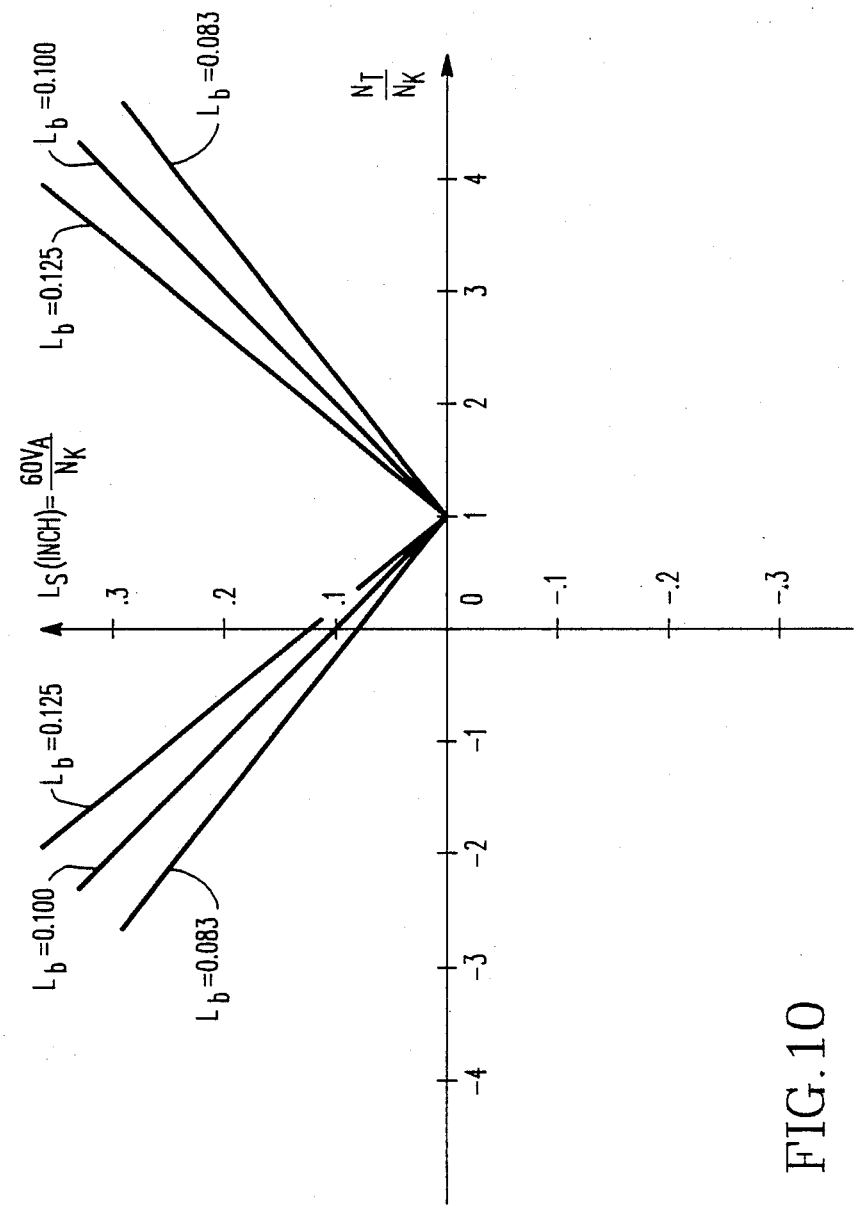
FIG. 10 graphically illustrates the inter-relationships of equations of motion describing the movement of the probe carrier and probe in the tube.

Referring to FIG. 10, there is shown a graph illustrating three specific examples of the relationship of Ls and Va/Nk as functions of the ratio (Nt/Nk) of the speeds of second reversible motor 420 and first reversible motor 400. The ordinate and abscissa in FIG. 10 segregates FIG. 10 into quadrants. Referring to the particularized equations of motion hereinabove and referring to the upper left-hand and right-hand quadrants of FIG. 10, it will be understood that for values of the ordinate less than one, the scan path is a right-hand helix and probe carrier advances in tube 71 if NK is positive or retreats in tube 71 if NK is negative. On the other hand, for values of the ordinate greater than one, the scan path is a left-hand helix and probe carrier 210 advances in tube 71 if NK is negative or retreats in tube 71 if NK is positive. Finally, for an ordinate value equal to one, Nt equals NK and there is no relative rotation between probe carrier 210 and second sleeve 490; hence, probe carrier 210 rotates in place, neither advancing nor retreating in tube 71.

Displaying the particularized equations of motion in graphical form provides a graphical means for conveniently determining the ratio Nt/Nk that corresponds to a desired Ls or Va/NK and for determining Ls or Va/NK corresponding to a desired ratio Nt/Nk. It is clear upon review of FIG. 10, that for each value of Lb there are two values of Nt/NK which may be selected to provide any desired scan lead, Ls. The value of Nt/NK to select for a desired Ls and Lb may be determined by considering whether a righthand or a left-hand helical scan path is required. By way of example, if Lb equal to 0.100 and Ls equal to 0.100 are desired, then a value of Nt/NK equal to zero or two may be selected. If Nt/NK equal to zero is selected, a right-hand helical scan path is provided. If Nt/NK equal to two is selected, a left-hand helical scan path is provided.

It will be appreciated that a value for Va may be obtained by using FIG. 10 to obtain Va/Nk for a desired ratio Nt/Nk and then multiplying Va/Nk by the known value for Nk to obtain Va. It should be evident from the above description that D is predetermined for a prespecified diameter of the scanning surface, which in this illustration is the inside diameter of tube 71. It should also be evident that Lb is predetermined for a given configuration of second sleeve 490. Therefore, for purposes of illustration in FIG. 10, Lb has been specifically selected as 0.083, 0.100 and 0.125 inch. Consequently, for a known Lb, a graph similar to FIG. 10 may be preconstructed by generating suitable values of Nt/Nk and solving the particularized equations of motion for Ls and Va/Nk and graphing the values of Ls and Va/Nk as a function of the ratio Nt/Nk. Hence, for a desired Ls the corresponding value of Nt/Nk can be obtained from FIG. 10 and used to set the relative speeds of second reversible motor 420 and first reversible motor 400 that would obtain the desired Ls. Alternatively, if it is desired to complete the inspection of tube 71 within a prespecified period of time, the required Nt/Nk is conveniently obtained from the preconstructed graph. That is, the desired distance along the axis of tube 71 that probe carrier 210 must travel is divided by the prespecified time to obtain the desired probe carrier speed Va. Next, Va is divided by a suitably selected Nk to obtain Va/Nk. FIG. 10 and Va/Nk may then be used to obtain the required ratio Nt/Nk associated with that Va/Nk. Of course, a graph similar to that shown in FIG. 10 need not be constructed; rather, either the basic equations of motion or the particularized equations of motion may be solved directly for the desired data in each specific case.

In order to use drive assembly 200, steam generator 20 is first drained of primary and secondary fluids. Service arm 230 may then be inserted through manway hole 170 and into inlet plenum chamber 130 or outlet plenum chamber 140 as necessary and releasibly engaged at one end of service arm 230 by camlock devices (not shown) to the ends of tubes 70 near tube 71, which is to be inspected. In this manner service arm 230 is releasibly secured beneath tube sheet 90. However, before service arm 230 is inserted through manway hole 170, the male coupler (not shown), may be attached to the other end of service arm 230 for releasibly coupling the male coupler to female coupler 250, which in turn is attached to flanged boss 240 belonging to drive assembly 200. Service arm 230 is manipulated by the operator such that drive assembly 200 is coaxially positioned beneath tube 71 and so that each expansion collar 300 of camlock apparatus 280 is inserted into an associated tube 70 proximate tube 71 to be inspected. Next, expansion collar 300 is expanded by operating camlock motor 320 such that expansion collar 300 expandably releasibly engages the inside surface of tube 70 near tube 71 for suspending drive assembly 200 beneath tube 71. After drive assembly 200 is suspended coaxially beneath tube 71, the operation of drive assembly 200 and the inspection of tube 71 may proceed.

A desired Ls or a desired Va/NK may be selected and the required ratio Nt/Nk corresponding to the desired Ls or Va may be calculated from the basic or particularized equations of motion described above. Alternatively, the required ratio Nt/Nk may be conveniently obtained as described above from a preconstructed graph similar to FIG. 10. The ratio of the speeds of second reversible motor 420 and first reversible motor 400 (Nt/Nk) are then set by the operator to obtain the desired Ls or Va/NK. As described in more detail hereinafter, setting the relative speeds of Nt and Nk determines the desired pitch and scanning pattern for probe 220.

Next probe carrier 210, having probe 220 attached thereto, may be advanced into tube 71 by operating second reversible motor 420. Operation of second reversible motor 420 rotates second sleeve 490 because, as stated above, second reversible motor 420 is operatively coupled to second sleeve 490. Operating second reversible motor 420 without operating first reversible motor 400 axially translates probe carrier 210 without rotation through second sleeve 490 due to the threaded engagement of internal threads 500 of second sleeve 490 and external threads 224 of probe carrier 210. Once inside tube 71, the operator may continue to advance probe carrier 210 in tube 71 without rotation of probe carrier 210 by operating second reversible motor 420 as described immediately above. Advancement of probe carrier 210 without rotation is equivalent to moving probe carrier 210 in a helical scanning path having a pitch obtaining an approximate value of infinity. Alternatively, once probe carrier 210 is advanced into tube 71, probe carrier 210 may be rotated in place by operating first reversible motor 400 at the same speed and with the same sense of rotation as the second reversible motor 420. Operation of first reversible motor 400 rotates first sleeve 444 because, as stated above, first reversible motor 400 is operatively coupled to first sleeve 444. Operating first reversible motor 400 and second reversible motor 420 at the same speed and with the same sense of rotation rotates probe carrier 210 without axial movement. Rotation of probe carrier 210 without axial movement is equivalent to moving probe carrier 210 in a helical scanning path having a pitch obtaining an approximate value of zero. Of course, the relative speeds Nt/Nk may be chosen in the manner described above and first reversible motor 400 and second reversible motor 420 may be cooperatively operated for obtaining a desired helical motion having a pitch between zero and infinity. Selection by the operator of the direction of rotation of first sleeve 444 determines whether probe 220 describes a righthand or a left-hand helical scanning pattern. Thus, by controlling the operation of first reversible motor 400 and second reversible motor 420, the operator controls the scanning pitch, the speed of helical motion, and the direction of helical motion. Drive assembly 200 therefore allows the operator reasonable control over the motion of probe 220, and thus the motion of the transducer connected thereto, so that probe 200 may gather the desired data regarding the physical characteristics of tube 71 at desired locations along tube 71.

When the inspection of tube 71 is complete, probe carrier 210 is retracted from tube 71 and drive assembly 200 is removed from steam generator 20 by a process that is essentially the reverse of inserting drive assembly 200 into steam generator 20 and the reverse of advancing probe carrier 210 into tube 71. In this regard, camlock apparatus 280 is disengaged from tube 70 in a manner that is generally the reverse of its initial engagement with tube 70. Service arm 230 is then used to remove drive assembly 200 from the vicinity of tube 71. Next, service arm 230 is unsecured from beneath tube sheet 90 by disengaging the camlock devices (not shown) from tube 70 and removing service arm 230 and drive assembly 200 from steam generator 20 through manway hole 170. Therefore, when the inspection of tube 71 is complete, drive assembly 200 may be withdrawn from steam generator 20 by a process which is essentially the reverse of inserting drive assembly 200 into steam generator 20. If the results of the inspection process described above indicate that tube 71 is not leak-tight, corrective action may be taken such as plugging or sleeving tube 71. It will be appreciated that the probe carrier drive assembly of the instant invention is capable of moving the probe carrier in a tube which may be either straight or curved. Moreover, drive assembly 200 is capable of moving the probe carrier in tube 71 such that the probe follows a helical scanning path of either righthand or left-hand orientation.

Figure 11:
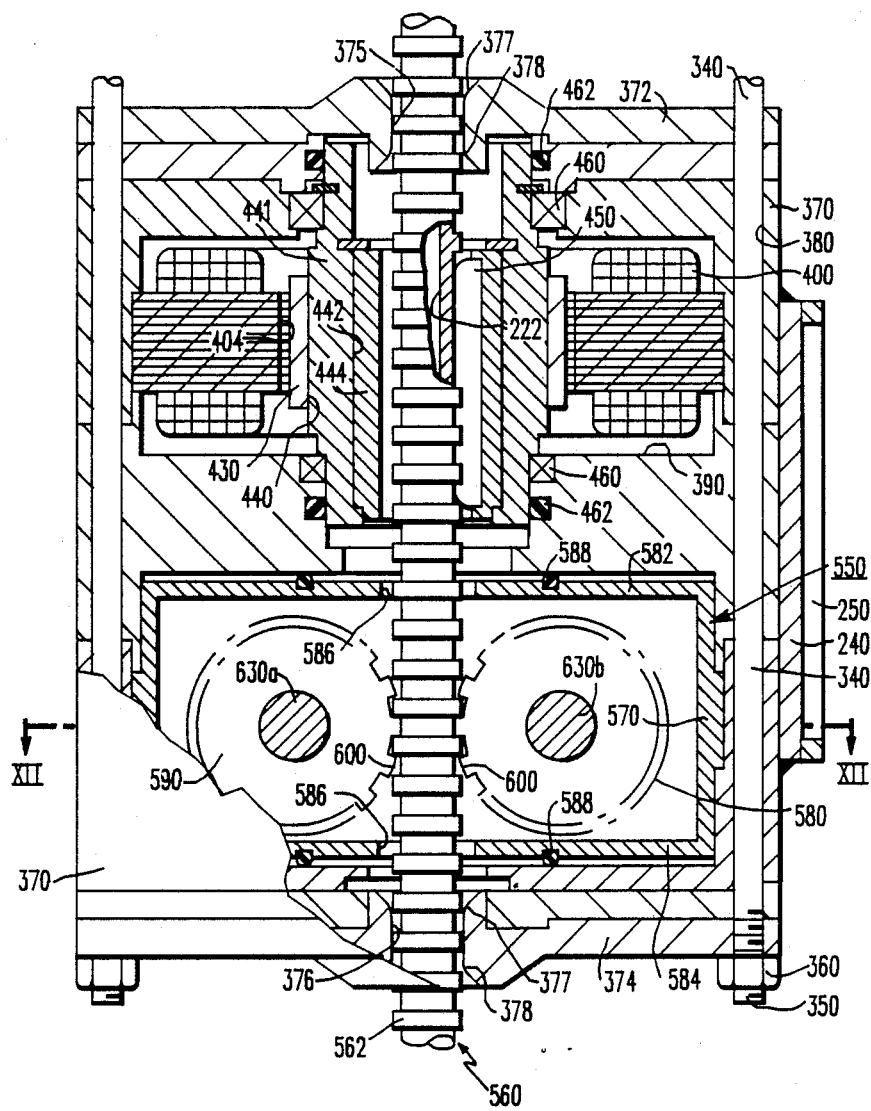
FIG. 11 shows in partial vertical section a second embodiment of the drive assembly which includes a high torque gear assembly disposed therein.
Figure 12:
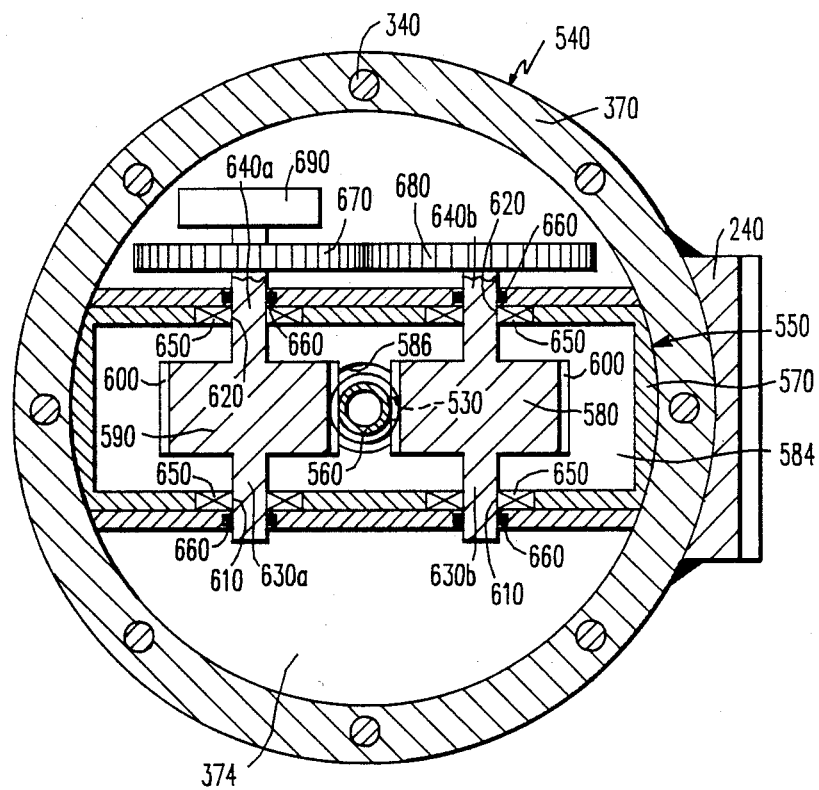
FIG. 12 is an illustration of the second embodiment of the drive assembly taken along section XII—XII of FIG. 11.

Referring to FIGS. 11 and 12, a second embodiment of the probe carrier drive assembly is generally referred to as 540. Drive assembly 540 is similar to drive assembly 200 except that a high torque gear assembly, which is generally referred to as 550 and which is disposed in drive assembly 540, is substituted for reversible motor 420, second rotor 470, second liner 481 and second sleeve 490 of drive assembly 200 (see FIGS. 5 and 11). Moreover, drive assembly 540 is similar to drive assembly 200 except that a high torque probe carrier, which is generally referred to as 560 is substituted for probe carrier 210 of drive assembly 200 (see FIGS. 5 and 11). High torque probe carrier 560 differs from probe carrier 210 at least with respect to high torque threads 562 integrally formed along the length of probe carrier 560. High torque threads 562, which surround probe carrier 560 along the length of probe carrier 560, obtain a nonhelical gear rack formation for transmitting a high torque to probe carrier 560. The gear rack formation of threads 562 enables probe carrier 560 to bear a greater torque than probe carrier 210 which has helical threads formed thereon. It will be understood that because probe carrier 560 can bear a higher torque than probe carrier 210, probe carrier 560 may be advanced or retracted through drive assembly 540 at a greater speed than may be possible when probe carrier 210 is used.

As illustrated in FIGS. 11 and 12, gear assembly 550 may comprise a generally rectangular gear assembly enclosure 570 for enclosing a first gear 580 and a second gear 590 therein. Enclosure 570 has a top plate 582 and a bottom plate 584 integrally attached thereto. Coaxially formed through top plate 582 and bottom plate 584 is an opening 586 for passage of probe carrier 560 therethrough. For the reasons stated below, enclosure 570 is sealed from the area surrounding enclosure 570 by first seal means 588 and second seal means 660 (see FIG. 12). First gear 580 and second gear 590 each includes a plurality of wide-faced gear teeth 600 distributed around the circumference of first gear 580 and the circumference of second gear 590. The wide-face of gear teeth 600 results in gear teeth 600 being sufficiently wide to straddle drive slot 530 which is formed through each thread 562 along the length of probe carrier 560. Formed in enclosure 570 are first ports 610 and second ports 620 for receiving the end portions of first gear shafts 630a and 630b and the end portions of second gear shafts 640a and 640b, respectively. Disposed in first ports 610 and second ports 620 and slidably contacting first gear shafts 630a and 630b and second gear shafts 640a and 640b are a plurality of gear shaft bearings 650 for reducing the amount of surface friction borne by the gear shafts when first gear shafts 630a and 630b and second gear shafts 640a and 640b rotate in first ports 610 and second ports 620, respectively. For the reasons stated below, also contacting first gear shafts 630a and 630b and second gear shafts 640a and 640b is second seal means 660 which cooperates with first seal means 588 for sealing enclosure 570 so that liquid which may be present in enclosure 570 does not leak into the area surrounding enclosure 570. Integrally attached to the terminal ends of second gear shafts 640a and 640b are a third gear 670 and a fourth gear 680, respectively. As best seen in FIG. 12, third gear 670 and fourth gear 680 are selected such that third gear 670 and fourth gear 680 matingly engage when third gear 670 is rotated by a reversible gear motor 690, which may be an electrical reversible gear motor, connected to third gear 670.

During operation of high torque gear assembly 550, fourth gear 680 and third gear 670 rotate in the same direction when third gear 670 is rotated by gear motor 690 due to the engagement of fourth gear 680 and third gear 670. It will be appreciated that gear motor 690 thus determines the direction of rotation of third gear 670 and fourth gear 680. It will be understood that first gear 580 and second gear 590 must rotate in the same direction as fourth gear 680 and third gear 670, respectively, because first gear 580 and second gear 590 are connected to fourth gear 680 and third gear 670, respectively, by gear shafts 640a and 640b. The gear teeth 600 of first gear 580 and second gear 590 engage high torque threads 562 of high torque probe carrier 560; therefore, high torque probe carrier 560 will advance or retreat as desired through drive assembly 540 depending on the direction of rotation of first gear 580 and second gear 590. As stated above, first seal means 588 and second seal means 660 cooperate to seal enclosure 570 from the area surrounding enclosure 570 so that liquid entering enclosure 570 through opening 586 does not leak from enclosure 570 into the area surrounding enclosure 570. Sealing enclosure 570 from the area surrounding enclosure 570 is desirable because if liquid from enclosure 570 were to contact motor 690, the performance of motor 690 might be degraded.

It will be appreciated that the basic equations of motion which describe the movement of high torque probe carrier 560 are different than the basic equations of motion which describe the movement of probe carrier 210. In the case of high torque probe carrier 560, the basic equations of motion are written as follows:

$$Ls' = \frac{Ng \pi Dp}{Nk} \tag{8}$$

$$Va' = \frac{Ng \pi Dp}{60} \text{ and} \tag{9}$$

$$Vs' = \sqrt{\left(\frac{Nk \pi D}{60}\right)^2 + \left(\frac{Ng \pi Dp}{60}\right)^2} \tag{10}$$

where,
Ng = rotational speed of first gear 580 in revolutions per minute;
Dp = pitch diameter of first gear 580;
Nk = rotational speed of first sleeve 444 in probe carrier drive assembly 540 in revolutions per minute;
Va' = speed of advance of high torque probe carrier 560 along the longitudinal axis of tube 71 in inches per second;
Vs' = surface speed of the impingement point of any scanning ray extending from the examination device to the surface of tube 71 in inches per second; and
D = diameter of the surface being scanned in inches.

It will also be understood from Equation (9) that the speed of advance or of retraction of high torque probe carrier 6560 is a function only of Ng. However, as indicated by Equation (10), the scan lead is a function of Ng and Nk.

Therefore, this invention provides a probe carrier drive assembly for moving a probe carrier without slip or creep in a steam generator tube so that the probe, which has an inspection device attached thereto and which is connected to the probe carrier, selectively rotates in place, follows a linear scanning path through the tube or follows a helical scanning path having a variable pitch.

What is claimed is:

1. A drive assembly for moving a probe carrier in a tubular member, comprising:
   (a) an elongated circular member having external threads therearound and having a drive slot extending through the threads;
   (b) drive means engaging the external threads and the drive slot of said elongated circular member for moving said elongated circular member axially and rotatably within the tubular member;
   (c) rotating means operatively coupled to said drive means for operating said drive means; and
   (d) controller means operatively coupled to said rotating means for operating said rotating means so that said elongated circular member selectively rotates in place, follows a linear path in the tubular member or follows a helical path having variable pitch.

2. The drive assembly acording to claim 1, wherein said elongated circular member is hollow for receiving electrical wires therethrough.

3. The drive assembly according to claim 1, wherein said drive means is a threaded linear drive means threadably engaging the external threads of said elongated circular member for axially moving said elongated circular member in the tubular member when the threads of said linear drive means threadably engage the external threads of said elongated circualr member.

4. The drive assembly according to claim 3, wherein said rotating means is a first rotating means operatively coupled to said linear drive means for operating said linear drive means so that said elongated circular member axially moves in the tubular member when said first rotating means operates said linear drive means.

5. The drive assembly according to claim 4, wherein said first rotating means is a first variable speed reversible motor.

6. The drive assembly according to claim 2, wherein the drive slot extends through the external threads along the longitudinal axis of said elongated circular member.

7. The drive assembly according to claim 6, wherein the drive slot extends from the top of each external thread to the base thereof.

8. The drive assembly according to claim 6, wherein said drive means is a rotary drive means matingly engaging the drive slot for rotatably moving said elongated circular member in the tubular member when said rotary drive means matingly engages the drive slot.

9. The drive assembly according to claim 8, wherein said rotating means is a second rotating means operatively coupled to said rotary drive means for operating said rotary drive means so that said elongated circular member rotates when said second rotating means operates said rotary drive means.

10. The drive assembly according to claim 9, wherein said second rotating means is a variable speed second reversible motor.

11. A probe carrier drive assembly for moving a probe carrier in a tube, comprising:
   (a) a drive shaft having external threads and having a longitudinal drive slot extending through the external threads along the longitudinal axis of said drive shaft;
   (b) a first sleeve surrounding a longitudinal portion of said drive shaft;
   (c) a rotary drive shaft insert integrally attached to the inside surface of said first sleeve, said drive shaft insert outwardly projecting from the inside surface of said first sleeve for rotatably matingly engaging the drive slot of said drive shaft and for rotating said drive shaft about the longitudinal axis thereof;
   (d) a second sleeve surrounding a different longitudinal portion of said drive shaft, said second sleeve having internal threads for matingly engaging the external threads of said drive shaft and for axially translating said drive shaft along the longitudinal axis of said tube;
   (e) first rotating means operatively coupled to said first sleeve for rotating said first sleeve;
   (f) second rotating means operatively coupled to said second sleeve for rotating said second sleeve; and
   (g) controller means operatively coupled to said first rotating means and to said second rotating means for selectively operating said first rotating means and said second rotating means so that said drive shaft selectively axially moves in the tube and rotatably moves in the tube, whereby said drive shaft selectively rotates in place, follows a linear path or follows a helical path having a variable pitch.

12. The drive assembly according to claim 11, wherein the drive slot extends from the top of each external thread to the base thereof.

13. The drive assembly according to claim 11, wherein said first rotating means is a variable speed first reversible motor.

14. The drive assembly according to claim 11, wherein said second rotating means is a variable speed second reversible motor.

15. The drive assembly according to claim 11, wherein said drive shaft is hollow for receiving electrical wires therethrough.

16. The drive assembly according to claim 11, further comprising a housing surrounding the drive assembly and connected thereto for enclosing the drive assembly therein.

17. The drive assembly according to claim 11, wherein the drive slot is a keyway longitudinally extending from near one end of said drive shaft to near the other end thereof for receiving said drive shaft insert.

18. The drive assembly according to claim 17, wherein said drive shaft insert is a key for matingly engaging the keyway.

19. The drive assembly according to claim 11, wherein the external threads are hexagonally-shaped for allowing a greater amount torque to be transferred by said first sleeve to the probe carrier.

20. The drive assembly according to claim 11, wherein the external threads are square-shaped for allowing a greater amount of torque to be transferred by said first sleeve to the probe carrier.

21. The drive assembly according to claim 11, wherein the external threads of said drive shaft are 29 degree stub tooth ACME threads for resisting abrasive wear on the distal ends of the external threads.

22. The drive assembly according to claim 11, wherein the internal threads are 29 degree stub tooth ACME threads for threadably engaging the external threads of said drive shaft.

23. A probe carrier drive assembly for moving a probe carrier in a steam generator tube, comprising:
   (a) a probe having a nondestructive examination scanning device attached thereto for nondestructively examining the tube, said probe capable of being inserted into the tube;
   (b) a hollow drive shaft connected to said probe for supporting said probe, said drive shaft having external threads thereon and having a drive slot formed through the external threads;
   (c) a first sleeve surrounding a longitudinal portion of said drive shaft;
   (d) a rotary drive shaft insert integrally attached to the inside surface of said first sleeve, said drive shaft insert outwardly projecting from the inside surface of said first sleeve for rotatably matingly engaging the drive slot of said drive shaft for rotating said drive shaft about the longitudinal axis of said drive shaft;
   (e) a second sleeve surrounding a different longitudinal portion of said drive shaft, said second sleeve having internal threads for matingly engaging the external threads of said drive shaft and for rotatably axially translating said drive shaft along the longitudinal axis of said tube, said second sleeve colinearly disposed with respect to said first sleeve;
   (f) a variable speed first reversible motor coupled to said first sleeve for rotating said first sleeve;
   (g) a variable speed second reversible motor coupled to said second sleeve for rotating said second sleeve;
   (h) a housing surrounding the drive assembly and connected thereto for enclosing said probe carrier drive assembly therein, said housing having an open front end and an open rear end for providing access to the inside of said housing and having at least two end cover plates for covering the open front end and the open rear end of said housing when the drive assembly is operating;
   (i) controller means operatively coupled to said first reversible motor and to said second reversible motor for selectively operating said first reversible motor and said second reversible motor so that said drive shaft selectively axially and rotatably moves in the steam generator tube, whereby the drive shaft selectively rotates in place, follows a linear scanning path through the steam generator tube or follows a helical scanning path having a variable pitch; and
   (j) support means connected to said housing, said support means capable of supporting said probe carrier drive assembly coaxially with respect to the tube.

24. The probe carrier drive assembly according to claim 23, wherein said probe further comprises at least one ultrasonic transducer attached thereto for inspecting the tube, said ultrasonic transducer having electrical wires, extending therefrom, the wires extending through the hollow portion of said drive shaft to a remote data analyzer for analyzing the electric impulses from the transducer so that the condition of the tube is inspected thereby.

25. The probe carrier drive assembly according to claim 23, wherein said probe is at least one eddy current coil for inspecting the tube, said eddy current coil having electrical wires extending therefrom, the wires extending through the hollow portion of said drive shaft to a remote data analyzer for analyzing the electric impulses from the eddy current coil so that the condition of the tube is inspected thereby.

26. The probe carrier drive assembly according to claim 23, wherein the drive slot is an elongated rectangle keyway longitudinally extending from near one end of said drive shaft to near the other end thereof.

27. The probe carrier drive assembly according to claim 26, wherein said drive shaft insert is an elongated rectangle key for matingly engaging the keyway.

28. The probe carrier drive assembly according to claim 23, wherein the external threads are hexagonally-shaped for allowing a greater amount of torque to be transferred by said first sleeve to the probe carrier.

29. The probe carrier drive assembly according to claim 23, wherein the external threads are square-shaped for allowing a greater amount of torque to be transferred by said first sleeve to the probe carrier.

30. The probe carrier drive assembly according to claim 23, wherein the external threads of said drive shaft are 29 degree stud tooth ACME threads for resisting abrasive wear on the distal ends of the external threads.

31. The probe carrier drive assembly according to claim 23, wherein the internal threads are 29 degree stub tooth ACME threads for threadably matingly engaging the external threads of said drive shaft.

32. The drive assembly according to claim 23, wherein said support means further comprises:
   (a) a base plate interposed between said housing and the tube, said base plate having a hole alignable with the longitudinal axis of the tube for receiving said probe and said drive shaft therethrough;
   (b) at least one spacer connecting said housing to said base plate and interposed therebetween for maintaining said base plate in spaced-apart relation with respect to said housing and for connecting said support means to said housing; and
   (c) at least one camlock apparatus having an expansion collar capable of releasibly expandably engaging the inside surface of a steam generator tube proximate the tube to be inspected, said camlock apparatus attached to said base plate for releasibly suspending the probe carrier drive assembly from a steam generator tube proximate the tube to inspected.

33. The probe carrier drive assembly according to claim 32, wherein said base plate is triangular for minimizing the volume of space occupied by said base plate.

* * * * *